US010588725B2

(12) United States Patent
Hagiwara et al.

(10) Patent No.: US 10,588,725 B2
(45) Date of Patent: Mar. 17, 2020

(54) STEREOLITHOGRAPHIC METHOD AND COMPOSITION

(71) Applicant: DWS S.R.L., Thiene (IT)

(72) Inventors: Tsuneo Hagiwara, Tokyo (JP); Satoshi Iketani, Vicenza (IT)

(73) Assignee: DWS S.R.L., Thiene (VI) (IT)

( * ) Notice: Subject to any disclaimer, the term of this patent is extended or adjusted under 35 U.S.C. 154(b) by 185 days.

(21) Appl. No.: 15/524,034

(22) PCT Filed: Oct. 30, 2015

(86) PCT No.: PCT/IB2015/058385
§ 371 (c)(1),
(2) Date: May 3, 2017

(87) PCT Pub. No.: WO2016/071811
PCT Pub. Date: May 12, 2016

(65) Prior Publication Data
US 2017/0333167 A1 Nov. 23, 2017

(30) Foreign Application Priority Data
Nov. 4, 2014 (IT) ................. VI2014A0285

(51) Int. Cl.
| | | |
|---|---|---|
| *C08F 2/46* | (2006.01) | |
| *C08F 2/50* | (2006.01) | |
| *C08G 61/04* | (2006.01) | |
| *A61C 13/00* | (2006.01) | |
| *G03F 7/00* | (2006.01) | |
| *C08G 83/00* | (2006.01) | |
| *C08B 37/16* | (2006.01) | |
| *A61K 6/09* | (2006.01) | |
| *C08L 5/16* | (2006.01) | |
| *G03F 7/038* | (2006.01) | |
| *G03F 7/20* | (2006.01) | |
| *B29C 64/135* | (2017.01) | |
| *G03F 7/027* | (2006.01) | |
| *A61C 13/087* | (2006.01) | |
| *A61K 6/00* | (2020.01) | |

(Continued)

(52) U.S. Cl.
CPC ...... *A61C 13/0013* (2013.01); *A61C 13/0004* (2013.01); *A61C 13/087* (2013.01); *A61K 6/0052* (2013.01); *A61K 6/083* (2013.01); *A61K 6/09* (2013.01); *B29C 64/135* (2017.08); *C08B 37/0015* (2013.01); *C08F 290/062* (2013.01); *C08F 290/068* (2013.01); *C08G 83/007* (2013.01); *C08L 5/16* (2013.01); *G03F 7/0037* (2013.01); *G03F 7/027* (2013.01); *G03F 7/029* (2013.01); *G03F 7/0388* (2013.01); *G03F 7/2012* (2013.01); *B33Y 10/00* (2014.12); *B33Y 70/00* (2014.12)

(58) Field of Classification Search
CPC . A61C 13/0013; A61C 13/004; A61C 13/087; G03F 7/0037; G03F 7/029; G03F 7/027; G03F 7/2012; G03F 7/0388; G03F 290/062; B29C 64/135; A61K 6/0052; A61K 6/083; A61K 6/09; C08F 290/062; C08F 290/068; C08F 7/027; C08B 27/0015; C08L 5/16; C08L 75/14; C08G 83/007; B33Y 70/00; B33Y 10/00
USPC .................................. 522/114, 113, 1; 520/1
See application file for complete search history.

(56) References Cited
U.S. PATENT DOCUMENTS

2002/0155189 A1* 10/2002 John ...................... B29C 64/129
425/174.4
2008/0306709 A1 12/2008 Fisker et al.
(Continued)

FOREIGN PATENT DOCUMENTS

| EP | 1734066 | 12/2006 |
|---|---|---|
| EP | 2787010 | 10/2017 |

(Continued)

OTHER PUBLICATIONS

Araki et al., "Recent advances in the prepration of cyclodextrin-based polyrotaxanes and their applications to soft materials," Soft Matter, 2007, 3, 1456-1473.
(Continued)

*Primary Examiner* — Jessica Whiteley
(74) *Attorney, Agent, or Firm* — Volpe and Koenig, P.C.

(57) ABSTRACT

The invention concerns a method for producing a three-dimensional object, in particular an artificial tooth, by stereolithography wherein a liquid photocurable resin composition is cured by light. Said photocurable resin composition contains, based on the total weight of the photocurable resin composition, (i) from 90 to 99.9% by weight of a radical polymerizable organic compound (A) selected from radical polymerizable monomers, oligomers, pre-polymers and mixtures thereof; and (ii) from 0.1 to 10% by weight of a photosensitive radical polymerization initiator (B). Said radical polymerizable organic compound (A) comprises, based on the weight of the radical polymerizable organic compound (A), from 0.5 to 20% by weight of a polyrotaxane compound comprising a polymer chain selected from polyethylene glycol (PEG), polypropylene glycol (PPG), polyethylene glycol-polypropylene glycol (PEG-PPG) block copolymer or polydimethylsiloxane (PDMS), onto which the cyclodextrin ring(s) is/are slipped and wherein the cyclodextrin is derivatized with at least a radical polymerizable group. The invention also concerns a relative liquid photocurable resin composition and articles produced thereby.

18 Claims, No Drawings

US 10,588,725 B2

Page 2

(51) Int. Cl.
*A61K 6/083* (2006.01)
*C08F 290/06* (2006.01)
*G03F 7/029* (2006.01)
*B33Y 70/00* (2020.01)
*B33Y 10/00* (2015.01)

(56) References Cited

U.S. PATENT DOCUMENTS

2009/0220916 A1   9/2009  Fisker et al.
2017/0335044 A1*  11/2017 Hayashi ................ C08F 2/48
2017/0360534 A1*  12/2017 Sun .................. A61C 13/0013

FOREIGN PATENT DOCUMENTS

| JP | S61185522 | 8/1986 |
| JP | H0215330 | 1/1990 |
| JP | 2000302964 | 10/2000 |
| JP | 2000351907 | 12/2000 |
| JP | 2011046917 | 3/2011 |
| JP | 2011085614 | 4/2011 |
| JP | 2013175277 | 9/2013 |
| WO | 2005095493 | 10/2005 |
| WO | 2011105532 | 9/2011 |
| WO | WO-2016072356 A1 * 5/2016 | ................ C08F 2/48 |

OTHER PUBLICATIONS

International Search Report regarding PCT/IB2015/058385, dated Jan. 26, 2016 (5 pgs.).
Written Opinion of the International Searching Authority regarding PCT/IB2015/058385, dated Jan. 26, 2016 (4 pgs.).

* cited by examiner

STEREOLITHOGRAPHIC METHOD AND COMPOSITION

TECHNICAL FIELD

The present invention relates to a stereolithographic manufacturing method using a photocurable resin composition which has especially been developed for stereolithography, to said photocurable resin composition and to a three-dimensional object produced therewith. More specifically, the present invention relates to a photocurable resin composition for stereolithography with which one can obtain a three-dimensional object with excellent dimensional precision with low volumetric shrinkage and furthermore having high toughness, high elasticity and excellent mechanical properties, a three-dimensional object produced therewith and a manufacturing method for producing said object using said photocurable resin composition.

STATE OF THE ART

In general, photocurable liquid resin compositions have been widely used as coating materials, photoresists and dental materials. In recent years, the layered manufacturing method based on the 3D-CAD data using photocurable resin compositions and a light source such as a laser beam has been the focus of attention because of its capacity of giving a highly accurate three-dimensional object.

For stereolithography technology, the method for producing a three-dimensional object by repeating the step of curing a thin layer by supplying a controlled amount of light energy to the photocurable liquid resin, supplying the photocurable liquid resin on that cured thin layer and curing another thin layer by supplying the controlled amount of light energy in the photocurable liquid resin, is disclosed by JP Patent publication no. 56-144478 and its basic practical methods have been proposed by JP Patent publication no. 60-247515. Since then, a number of proposals relating to stereolithography technology have been made.

As a typical method of producing optically a three-dimensional object, the method for producing a three-dimensional object by repeating a laminating operation of selectively irradiating with a computer-controlled UV laser beam on the surface of a photocurable liquid composition accommodated in a shaping container from above to sequentially form a cured resin layer of desired thickness is widely known and employed in general. This method has attracted a great deal of attention in recent years because, according to this method, a three-dimensional object of interest can be made easily and in a relatively short time even if the shape of the object is fairly complex. Meanwhile, the present inventors have proposed to get artificial teeth curing layer by layer a liquid dental photocurable resin composition irradiated with light converted to a spot shape using a line drawing system of linearly moving through the light permeable bottom face of a shaping container to form a cured resin layer, or a liquid dental photocurable resin composition irradiated planarly with light passed through a planar drawing mask formed by arranging a plurality of micro-optical shutters through the light permeable bottom face of the shaping container as described in JP Patent application no. 2013-175277. As a photocurable resin composition for coating materials, photoresists and dental materials, a material obtained by adding a photopolymerization initiator to curable resin materials such as unsaturated polyesters, epoxy (meth)acrylate compounds, urethane (meth)acrylate compounds, (meth)acrylate compounds is widely used.

Furthermore, as a photocurable resin composition for stereolithography, a material obtained by adding a photopolymerization initiator to a mixture of one or two or more of curable resin materials such as epoxy (meth)acrylate compounds, urethane (meth)acrylate compounds, (meth)acrylate compounds, oligoester (meth)acrylate compounds, epoxy compounds is widely used.

Patent documents JP 2011/85614 A, US 2008/0,306,709 A and US 2009/0,220,916 A describe the production of tooth models and artificial teeth.

The photocurable resin compound for stereolithography, in the view of handling, modelling speed and model accuracy, is needed to be a low viscosity liquid that gives low shrinkage and good mechanical properties after curing. Recently, with the boom of three-dimensional layered manufacturing (3D printer), the use and demand for three-dimensional objects is expanding dramatically. Accordingly, three-dimensional objects with high toughness and high elasticity are required for functional parts, and various strategies have been taken for that purpose.

The Applicant proposed in JP Patent application no. 2013-175277 liquid photocurable resin compositions which are in particular suitable for the production of artificial teeth. In a preferred embodiment, the composition contains, as at least a part of the photocurable resin composition consisting essentially of a radical polymerizable organic compound, at least one of a urethane-based di(meth)acrylate compound (A-1a) obtained by the reaction of 1 mol of an organic diisocyanate compound with 2 mol of hydroxyalkyl(meth)acrylate, represented by the following general formula (A-1a):

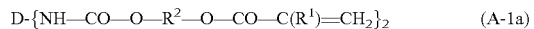

$$D-\{NH-CO-O-R^2-O-CO-C(R^1)=CH_2\}_2 \quad (A-1a)$$

wherein $R^1$ represents a hydrogen atom or a methyl group, $R^2$ represents an alkylene group, and D represents an organic diisocyanate compound residue; and a di(meth)acrylate compound (A-1b) obtained by the reaction of 1 mol of a diepoxy compound with 2 mol of (meth)acrylic acid, represented by the following general formula (A-1b):

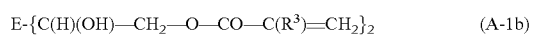

$$E-\{C(H)(OH)-CH_2-O-CO-C(R^3)=CH_2\}_2 \quad (A-1b)$$

wherein $R^3$ represents a hydrogen atom or a methyl group, and E represents a diepoxy compound residue.

In order to further improve the durability of the artificial teeth proposed, it is required to give to the material high toughness and high elasticity to avoid the breakage even if inadvertent force is applied during wear.

For the production of a three-dimensional object made by stereolithography having a high modulus of elasticity with high toughness, it is known a method to make a three-dimensional object with a photocurable resin containing rubber polymer particles (JP 2000-302964, JP 2000-351907). However, this method has the disadvantage that the viscosity of the resin composition becomes high because it is blended with the rubber polymer particles in the photocurable resin, so the modelling accuracy and handling property are decreased. Further, a urethane acrylate resin composition containing caprolactone units is known for the purpose of obtaining high toughness and improving tensile elongation (JP 61-185522) but only tensile elongation can be improved to some extent and the balance of mechanical strength and toughness cannot be said to be sufficient.

Improving the performance of the artificial teeth also means improving the performance of a three-dimensional object made by stereolithography in general and means that the stereoscopically shaped three-dimensional objects provide sufficient performance as prototypes or final products.

PRESENTATION OF THE INVENTION

Problems to be Solved by the Invention

An object of the present invention is to provide a method of producing three-dimensional objects, in particular artificial teeth, and a corresponding photocurable resin composition to be employed in this method with which one can obtain a three-dimensional object in a short time with excellent dimensional precision with low volumetric shrinkage and furthermore having high toughness, high elasticity and excellent mechanical properties.

Another object of the present invention is to provide artificial teeth produced with said resin composition and/or obtained by the stereolithographic method and having excellent strength and toughness.

Means for Solving the Problems

The present inventors have intensively studied so as to achieve the above objects. As a result, they have found that a polyrotaxane compound bearing photo-crosslinkable groups, preferably methacryloyl-based groups, in combination with other radical polymerizable compounds and a photopolymerization initiator as defined in claim 1 is highly effective in achieving the above objects and particularly suited for stereolithographic processes as it represents a low viscosity with excellent handling properties and as this photocurable resin composition can be cured in a short time by irradiating with light.

It has been found that a three-dimensional object with excellent dimensional precision and low volumetric shrinkage and furthermore having high toughness, high elasticity and excellent mechanical properties is obtained using this photocurable resin composition in stereolithography. Furthermore, it has been found that employing this photocurable resin composition in stereolithography to manufacture artificial teeth, artificial teeth with good durability, excellent dimensional accuracy, high mechanical strength, high toughness and excellent aesthetics can be obtained.

The polyrotaxane, a supermolecular compound that has attracted attention in recent years, is a molecule wherein a number of nanosized rings, for example cyclodextrins, are penetrated by linear polymers such as a polyethylene glycol chain. In general, several cyclodextrin rings are slipped onto a polyethylene glycol (PEG) chain which is capped by bulky groups, such as adamantane amine residues, avoiding the slipping off of the rings. Polyrotaxanes have been intensively studied in detail by J. Araki, K. Ito et. al. in Soft Matter 2007, 2, 1456-1473. By adding this polyrotaxane to other polymeric materials, "movable cross-linking points" are present in the material. It is said that this movable cross-linking points, which can be moved to the optimum position when stress is applied, bring revolutionary effects such as reinforcing effect, high swelling index and high expansion rate, etc. on the material. The starting materials of the polyrotaxane manufacturing are mainly polyethylene glycol (PEG) and α-cyclodextrin which is a cyclic oligosaccharide, both having high biological safety and applications of polyrotaxane are proceedings in medical applications.

In addition, in the publication WO 2005/095493, cross-linking polyrotaxane compositions containing, as crosslinkable polymer, polyrotaxane and other photocrosslinking groups such as cinnamic acid, coumarin, chalcone, anthracene, styrylpyridine, styrylpyridinium salt, styrylquinolium salt are disclosed. In this publication the creation of such as an aqueous gel has been proposed and its technical scope is quite different from the photocurable composition for stereolithography according to the invention. And in the documents WO 2011/105532 and JP 2011-046917, crosslinking polyrotaxane compositions containing acrylate group, styryl group, vinyl ether group, maleimide group are disclosed. These crosslinking groups are introduced into the polyrotaxane by polymer reaction. In particular, polyrotaxanes obtained by introducing acrylate groups have been described. In said publication, the method of improving the resistance to damages by scratch using this photo-crosslinkable polyrotaxane compound, which is composed from a photo-crosslinkable polymer compound and a photopolymerization initiator, is described but it is silent about any technical disclosure regarding the use of such a photocurable composition for stereolithography. Furthermore, there is no description of photocurable resin compositions containing photo-crosslinkable acrylate monomers suitable for stereolithography, which is a main object of the present invention, and there is no description of the light curing properties of layered manufacturing.

In the present invention, by adding a certain percentage of the polyrotaxane compound that has been modified for example with (meth)acrylic groups as photoreactive group to another radically polymerizable compound, it is possible to improve dramatically the mechanical properties of the cured material so the performance of the shaped object without compromising the original performance as photocurable composition.

Thus, in a first aspect, the present invention is directed to a method for producing a three-dimensional object, in particular an artificial tooth, by stereolithography wherein a liquid photocurable resin composition is cured by light, said photocurable resin composition containing:

(i) from 90 to 99.9% by weight, based on the total weight of the photocurable resin composition, of a radical polymerizable organic compound (A) selected from radical polymerizable monomers, oligomers, pre-polymers and mixtures thereof;

(ii) from 0.1 to 10% by weight, based on the total weight of the photocurable resin composition, of a photosensitive radical polymerization initiator (B);

wherein said radical polymerizable organic compound (A) comprises, based on the weight of the radical polymerizable organic compound (A), from 0.5 to 20% by weight of a polyrotaxane compound having the following general formula (I):

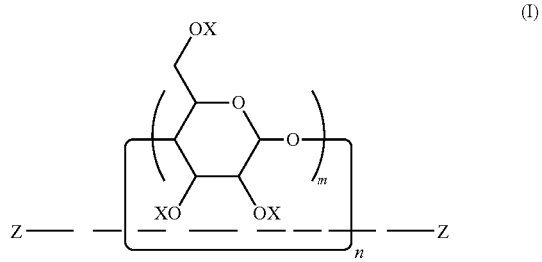

wherein
Z is a bulky capping group, preferably selected from adamantane and its derivatives, 2,4-dinitrophenyl, or cyclodextrin and its derivatives;
the dotted line ------ is a polymer chain selected from the group consisting of polyethylene glycol (PEG), polypropylene glycol (PPG), polyethylene glycol-polypropylene glycol (PEG-PPG) block copolymer or polydimethylsiloxane (PDMS), onto which the cyclodextrin ring(s) is/are slipped;
m is an integer and independently represents the number of glucose units in the cyclodextrin ring, preferably m=6, 7 or 8;
n is an integer and represents the number of cyclodextrin rings;
X is independently H, or a radical polymerizable group, such as a methacryloyl-containing or an acryloyl-containing group, with the condition that at least one X is a radical polymerizable group.

The method according to the invention permits the production of three-dimensional objects with excellent properties, as already discussed above, thanks to the characteristics provided by the improved photo-curable resin composition.

In fact, another aspect of the present invention is a liquid photocurable resin composition for stereolithography, containing:
(i) from 90 to 99.9% by weight, based on the total weight of the photocurable resin composition, of a radical polymerizable organic compound (A) selected from radical polymerizable monomers, oligomers, pre-polymers and mixtures thereof;
(ii) from 0.1 to 10% by weight, based on the total weight of the photocurable resin composition, of a photosensitive radical polymerization initiator (B);
wherein said radical polymerizable organic compound (A) comprises, based on the weight of the radical polymerizable organic compound (A), from 0.5 to 20% by weight of a polyrotaxane compound having the following general formula (I):

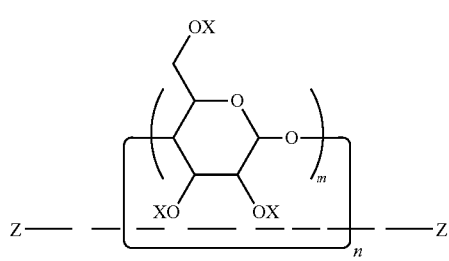

wherein
Z is a bulky capping group, preferably selected from adamantane and its derivatives, 2,4-dinitrophenyl, or cyclodextrin and its derivatives;
the dotted line ------ is a polymer chain selected from the group consisting of polyethylene glycol (PEG), polypropylene glycol (PPG), polyethylene glycol-polypropylene glycol (PEG-PPG) block copolymer or polydimethylsiloxane (PDMS), onto which the cyclodextrin ring(s) is/are slipped;
m is an integer and independently represents the number of glucose units in the cyclodextrin ring, preferably m=6, 7 or 8;
n is an integer and represents the number of cyclodextrin rings;
X is independently H, or a radical polymerizable group, such as a methacryloyl-containing or an acryloyl-containing group, with the condition that at least one X is a radical polymerizable group.
α-cyclodextrin (m=6) is preferred if the polymer chain is polyethylene glycol, β-cyclodextrin (m=7) is preferred if the polymer chain is polypropylene glycol, and γ-cyclodextrin (m=8) is preferred if the polymer chain is polydimethylsiloxane. The number of cyclodextrin rings is of minor importance; preferred values are, however, n=30-100.

It is possible to use, as the photosensitive radical polymerization initiator (B) in the photocurable resin composition according to the present invention, any polymerization initiator capable of initiating radical polymerization of the radical polymerizable organic compound (A) when irradiated with light.

Specific examples of the photosensitive radical polymerization initiator (B) usable in the present invention include, but are not limited to, benzoin ether compounds such as benzoin ethyl ether, benzoin isopropyl ether, and benzoin phenyl ether; acetophenone compounds such as acetophenone, 2,2-dimethoxyacetophenone and 1,1-dichloroacetophenone; benzyl ketal compounds such as benzyl dimethyl ketal and benzyl diethyl ketal; anthraquinone compounds such as 2-methylanthraquinone, 2-ethylalkylanthraquinone, 2-tertiary-butylanthraquinone, 1-chloroanthraquinone and 2-amylanthraquinone; phosphine compounds such as triphenylphosphine; benzoylphosphine oxide compounds such as 2,4,6-trimethylbenzoyl-diphenyl-phosphine oxide (Irgacure TPO); bisacylphosphine oxide compounds such as bis(2,4,6-trimethylbenzoyl)-phenylphosphine oxide (Irgacure 819); benzophenone compounds such as benzophenone and 4,4'-bis(N,N'-dimethylamino)benzophenone; thioxanthone and xanthone; acridine derivatives; fenadine derivatives; quinoxaline derivatives; 1-phenyl-1,2-propanedion and 2-O-benzoyloxime; 4-(2-hydroxyethoxy)phenyl-(2-propyl)ketone (Irgacure 2959); 1-aminophenyl ketones or 1-hydroxyphenyl ketones, such as 1-hydroxycyclohexyl phenyl ketone, 2-hydroxyisopropyl phenyl ketone, phenyl 1-hydroxyisopropyl ketone, and 4-isopropylphenyl 1-hydroxyisopropyl ketone; and the like.

Of the photosensitive radical polymerization initiators mentioned above, benzoylphosphine oxide such as 2,4,6-trimethylbenzoyl-diphenylphosphine oxide (Irgacure TPO) and bisacylphosphine oxide (Irgacure 819) is preferably used as the photosensitive radical polymerization initiator (B) in view of the fact that the dental photocurable resin composition used in the present invention is capable of satisfactory photocuring under ultraviolet light, near ultraviolet light, and short-wavelength visible light.

Further embodiments and characteristics of the resin composition according to the invention are explained in the following pages. They apply mutatis mutandis to the stereolithographic method since it is the resin composition according to the invention in all its embodiments which can be used/cured in the method according to the invention.

The polyrotaxane compound as defined in the claims shows the effect of the present invention when it is contained in a proportion of 0.5 to 20% by weight based on the weight of the radical polymerizable organic compound (A). In a preferred embodiment of the invention, it is contained in a proportion of 1 to 15% by weight. In the case of less than 0.5% by weight it is impossible to get the benefits of high elasticity and high toughness from the polyrotaxane compound. Moreover, if the amount is greater than 20% by weight, the viscosity of the photocurable resin composition becomes extremely high and it becomes impossible to use it for the purpose of the invention.

In a preferred embodiment of the invention, said radical polymerizable group is constituted by a methacryloyl or acryloyl-containing unit bonded by a spacer unit to said cyclodextrin ring. EP 1 734 066 A1 and WO 2011/05532 A1 offer a lot of possible production methods to obtain such modified polyrotaxane compounds. For example, the radical polymerizable group of the polyrotaxane compound can be a methacryloyl or acryloyl-containing group obtained by reacting a hydroxyl group of a spacer molecule bonded to a hydroxyl group of said cyclodextrin ring with $CH_2=C(R^1)CO_2(CH_2)_2NCO$, wherein $R^1$ represents a hydrogen atom or a methyl group, wherein the spacer unit is independently selected from $—[(C=O)(CH_2)_5O—]_p—H$ or $H—[O(CH_2)_5(C=O)]_qOCH(Me)CH_2—$ with p and q being integers indicating the number of repeating units. Preferred spacer units are caprolactone-based. Document WO 2011/105532 A1 describes the polycaprolactone-modification of (hydroxypropyl)cyclodextrin rings of polyrotaxane molecules and the introduction of a (meth)acryloyl group to the polycaprolactone chain.

Preferably, the radical polymerizable group is independently selected from

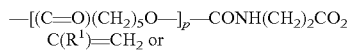
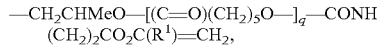

wherein $R^1$ represents a hydrogen atom or a methyl group with p and q being integers indicating the number of repeating units.

Preferred average values for p and q are 3-4. In an advantageous embodiment of the invention, in a cyclodextrin ring two hydroxyl groups have been derivatized with a photo-crosslinkable group, in particular the cyclodextrin rings bears a

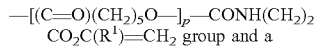
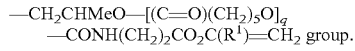

Preferably, the viscosity of said photocurable resin composition is 20,000 mPa·s or less, more preferably 15,000 mPa·s or less, and still more preferably 10,000 mPa·s or less, when measured at 25° C. according to method ISO 2555 with a single cylinder rotational viscometer. A low viscosity guarantees optimal resin properties in terms of handling, modeling speed and model accuracy in the stereolithographic process. The viscosity of the dental photocurable resin composition can be controlled by selecting kinds and combinations of the radical polymerizable organic compound (A), kinds and average particle diameters of a possible filler (C), mixing ratios of the radical polymerizable organic compound (A) and the filler (C), and the like.

In another advantageous embodiment of the invention, said radical polymerizable organic compound (A) further comprises:
(i) a urethane-based di(meth)acrylate compound (A-1a) obtained by the reaction of 1 mol of an organic diisocyanate compound with 2 mol of hydroxyalkyl (meth)acrylate, represented by the following general formula (A-1a):

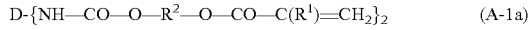

wherein $R^1$ represents a hydrogen atom or a methyl group, $R^2$ represents an alkylene group, and D represents an organic diisocyanate compound residue; and/or
(ii) a di(meth)acrylate compound (A-1b) obtained by the reaction of 1 mol of a diepoxy compound with 2 mol of (meth)acrylic acid, represented by the following general formula (A-1b):

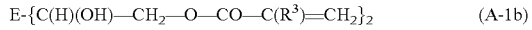

wherein $R^3$ represents a hydrogen atom or a methyl group, and E represents a diepoxy compound residue.

The radical polymerizable organic compound (A) used in the photocurable resin composition of the present invention is preferably configured totally by acrylate compounds or totally by methacrylate compounds uniformly. It often becomes difficult to obtain a cured product having desired physical properties if the reaction system is disturbed by mixing a methacrylate compound and acrylate compound.

Furthermore, in the radical polymerizable organic compound (A) of the present invention containing the polyrotaxane compound with a radical polymerizable group and a urethane-based di(meth)acrylate compound (A-1a) and/or a di(meth)acrylate compound (A-1b), the content of the polyrotaxane compound (I) is preferably 0.5 to 20% by weight based on the weight of the radical polymerizable organic compound (A).

Preferably, the radical polymerizable organic compound (A) is exclusively methacrylate-based. When the three-dimensional object made from the composition is an artificial tooth or an object that comes into contact with the human body, a compound (A) having a methacrylic group is preferable as compared with a compound having an acrylic group in view of biocompatibility. It is possible to use, as the radical polymerizable organic compound (A) other than the polyrotaxane compound in the photocurable resin composition, any radical polymerizable organic compound as long as it is usable as a photocurable resin material. In view of availability and reactivity, a (meth)acrylic compound having one or two or more acrylic group(s) and/or methacrylic group(s) in a molecule is preferably used.

Of these compounds, the photocurable resin composition used in the present invention preferably contains, as a portion of the radical polymerizable organic compound (A),
(i) at least one of a urethane-based di(meth)acrylate compound (A-1a) obtained by the reaction of 1 mol of an organic diisocyanate compound with 2 mol of hydroxyalkyl (meth)acrylate, represented by the following general formula (A-1a):

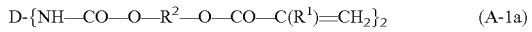

wherein $R^1$ represents a hydrogen atom or a methyl group, $R^2$ represents an alkylene group, and D represents an organic diisocyanate compound residue (group after removing two isocyanate groups from organic diisocyanate compound); and
(ii) a di(meth)acrylate compound (A-1 b) obtained by the reaction of 1 mol of a diepoxy compound with 2 mol of (meth)acrylic acid, represented by the following general formula (A-1 b):

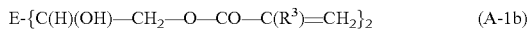

wherein $R^3$ represents a hydrogen atom or a methyl group, and E represents a diepoxy compound residue (group after removing two epoxy groups from diepoxy compound), in view of compatibility with the human body, ease of availability, mechanical properties, and the like.

The resin composition according to the present invention may contain either or both of the following compounds: a urethane-based di(meth)acrylate compound (A-1a) and a di(meth)acrylate compound (A-1b).

And the content (the total content when both compounds are contained) of at least one of the urethane-based di(meth)acrylate compound (A-1a) and one of the di(meth)acrylate compound (A-1b) is preferably 5 to 95% by weight, more preferably 20 to 80% by weight, and still more preferably 30 to 70% by weight, based on the weight of the radical polymerizable organic compound (A).

When the radical polymerizable organic compound (A) is the composition as described above, the three-dimensional object obtained by stereolithography has excellent mechanical properties.

In the above general formula (A-1a), the organic diisocyanate compound residue D may be any of an aromatic diisocyanate compound residue, an aliphatic diisocyanate compound residue, and an alicyclic diisocyanate compound residue.

Examples of the urethane-based di(meth)acrylate-based compound (A-1a) include, but are not limited to, urethane di(meth)acrylates obtained by the reaction of 1 mol of an organic diisocyanate compound composed of one, or two or more aliphatic diisocyanate compound(s) such as hexamethylene diisocyanate, 2,2,4-trimethylhexamethylene diisocyanate, isophorone diisocyanate, hydrogenated diphenylmethane diisocyanate, hydrogenated m-xylylene diisocyanate, and hydrogenated toluene diisocyanate, and aromatic diisocyanates such as diphenylmethane diisocyanate, toluene diisocyanate, and xylylene diisocyanate with 2 mol of a hydroxyalkyl ester whose (meth)acrylic acid has 2 to 6 carbon atoms, such as hydroxyethyl (meth)acrylate, hydroxypropyl (meth)acrylate, hydroxybutyl (meth)acrylate, hydroxypentyl (meth)acrylate and hydroxyhexyl (meth)acrylate [(meth)acrylic acid ester obtained by the reaction of 1 mol of an alkylenediol having 2 to 6 carbon atoms with 1 mol of (meth)acrylic acid].

More specific examples thereof include urethane di(meth)acrylate obtained by reacting 1 mol of 2,2,4-trimethylhexamethylene diisocyanate with 2 mol of hydroxyethyl (meth)acrylate, urethane di(meth)acrylate obtained by reacting 1 mol of isophorone diisocyanate with 2 mol of hydroxyethyl (meth)acrylate, urethane di(meth)acrylate obtained by reacting 1 mol of hydrogenated diphenylmethane diisocyanate with 2 mol of hydroxyethyl (meth)acrylate, urethane di(meth)acrylate obtained by reacting 1 mol of 2,2,4-trimethylhexamethylene diisocyanate with 2 mol of hydroxypropyl (meth)acrylate, urethane di(meth)acrylate obtained by reacting 1 mol of isophorone diisocyanate with 2 mol of hydroxypropyl (meth)acrylate, urethane di(meth)acrylate obtained by reacting 1 mol of 2,2,4-trimethylhexamethylene diisocyanate with 2 mol of hydroxyethyl (meth)acrylate, urethane di(meth)acrylate obtained by reacting 1 mol of diphenylmethane diisocyanate with 2 mol of hydroxyethyl (meth)acrylate, urethane di(meth)acrylate obtained by reacting 1 mol of diphenylmethane diisocyanate with 2 mol of hydroxypropyl (meth)acrylate, urethane di(meth)acrylate obtained by reacting 1 mol of toluene diisocyanate with 2 mol of hydroxyethyl (meth)acrylate, urethane di(meth)acrylate obtained by reacting 1 mol of toluene diisocyanate with 2 mol of hydroxypropyl (meth)acrylate, and the like, and one, or two or more urethane di(meth)acrylate(s) can be used.

Of these compounds, urethane dimethacrylate obtained by reacting 1 mol of 2,2,4-trimethylhexamethylene diisocyanate with 2 mol of hydroxyethyl methacrylate, so-called UDMA, is preferably used as the urethane-based di(meth)acrylate compound (A-1a) in view of availability, mechanical properties and compatibility with the human body.

In the above general formula (A-1b), the diepoxy compound residue E may be any of an aromatic diepoxy compound residue, an aliphatic diepoxy compound residue, and an alicyclic diepoxy compound residue.

Non-limiting examples of the di(meth)acrylate compound (A-1b) include a di(meth)acrylate compound obtained by reacting 1 mol of a diepoxy compound composed of one, or two or more aromatic diepoxy compound(s), alicyclic diepoxy compound(s), and aliphatic diepoxy compound(s) with 2 mol of (meth)acrylic acid, and a di(meth)acrylate compound obtained by reacting 1 mol of an aromatic diepoxy compound with 2 mol of (meth)acrylic acid is preferably used in view of availability, mechanical properties and compatibility with the human body.

Specific examples thereof include a di(meth)acrylate compound obtained by reacting 1 mol of diglycidyl ether of a bisphenol-based compound such as bisphenol A or bisphenol F with 2 mol of (meth)acrylic acid, a di(meth)acrylate compound obtained by reacting 1 mol of diglycidyl ether, which is obtained by reacting an alkylene oxide adduct of a bisphenol-based compound such as bisphenol A or bisphenol F with an epoxydating agent such as epichlorohydrin, with 2 mol of (meth)acrylic acid, a di(meth)acrylate compound obtained by reacting 1 mol of a novolake type diepoxy compound with 2 mol of (meth)acrylic acid, and the like, and one, or two or more di(meth)acrylate compound(s) can be used.

Of these di(meth)acrylate compounds, a dimethacrylate compound obtained by reacting 1 mol of diglycidyl ether, which is obtained by reacting a bisphenol A compound with epichlorohydrin, with 2 mol of methacrylic acid, so-called BisGMA, is preferably used as the epoxy-based di(meth)acrylate compound (A-1 b) in view of availability, mechanical properties and compatibility with the human body.

Advantageously, every radical polymerizable organic compound (A) is a methacrylate-based compound.

In a particularly preferred embodiment of the invention, in said polyrotaxane compound the polymer chain is polyethylene glycol, the cyclodextrin is α-cyclodextrin and the bulky groups are —NH-adamantane.

The liquid photocurable resin composition used in the present invention can optionally further contain another radical polymerizable organic compound (A-2), as part of the radical polymerizable organic compound (A) which acts as a viscosity reducing compound. Preferably it is present together with at least one of a urethane-based di(meth)acrylate compound (A-1a) and a di(meth)acrylate compound (A-1b).

It is possible to adjust the viscosity of the dental photocurable resin composition to the value suited for stereolithography by including the other radical polymerizable organic compound (A-2), in particular together with at least one of a urethane-based di(meth)acrylate compound (A-1a) and a di(meth)acrylate compound (A-1b).

Preferably, said viscosity reducing compound (A-2) is at least one of a methacrylic acid ester, an acrylic acid ester, a polyester methacrylate, a polyester acrylate, a polyether methacrylate of alcohols, a polyether acrylate of alcohols.

Further, if the radical polymerizable organic compound (A) of the present invention contains the other radical polymerizable organic compound (A-2) other than the polyrotaxane compound (I), a urethane-based di(meth)acrylate compound (A-1a) and a di(meth)acrylate compound (A-1b), the content of the other radical polymerizable organic compound (A-2) is preferably 4 to 90% by weight, more preferably 10 to 79% by weight, and still more preferably 15 to 69% by weight, based on the weight of the radical polymerizable organic compound (A). When the content of the other radical polymerizable organic compound (A-2) is within the above range, it is possible to obtain the effect of an improvement in reactivity, together with the effect of a decrease in viscosity of a photocurable resin composition.

It is possible to use, as the other radical polymerizable organic compound (A-2), any radical polymerizable organic compound which has hitherto been used in a resin composition for stereolithography and, typically, a compound having at least one (meth)acrylic group in a molecule is preferably used, and specific examples thereof include a (meth)acrylic acid ester, polyester (meth)acrylate, polyether (meth)acrylate of alcohols, and the like.

Examples of the (meth)acrylic acid ester of alcohols include a (meth)acrylic acid ester obtained by reacting an aromatic group-containing alcohol having at least one hydroxyl group in the molecule, an aliphatic alcohol, an alicyclic alcohol, or an alkylene oxide adduct of certain alcohols mentioned above with (meth)acrylic acid, and one, or two or more thereof can be used.

More specific examples of the other radical polymerizable organic compound (A-2) include 2-ethylhexyl (meth)acrylate, 2-hydroxyethyl (meth)acrylate, 2-hydroxypropyl (meth)acrylate, lauryl (meth)acrylate, stearyl (meth)acrylate, isooctyl (meth)acrylate, tetrahydrofurfuryl (meth)acrylate, isobornyl (meth)acrylate, benzyl (meth)acrylate, 1,4-butanediol di(meth)acrylate, 1,6-hexanediol di(meth)acrylate, diethylene glycol di(meth)acrylate, triethylene glycol di(meth)acrylate, neopentyl glycol di(meth)acrylate, polyethylene glycol di(meth)acrylate, polypropylene glycol di(meth)acrylate, trimethylolpropane tri(meth)acrylate, pentaerythritol tetra(meth)acrylate, dipentaerythritol hexa(meth)acrylate and the other dipentaerythritol poly(meth)acrylate, (meth)acrylate of an alkylene oxide adduct of the polyhydric alcohols mentioned above such as diol, triol, tetraol, or hexaol, ethylene oxide-modified bisphenol A diacrylate, propylene oxide-modified bisphenol A diacrylate, and the like.

Of these compounds, (meth)acrylate having two or more (meth)acrylic groups in a molecule obtained by the reaction of a dihydric alcohol or a tri- or higher polyhydric alcohol with (meth)acrylic acid is preferably used as the other radical polymerizable organic compound (A-2) in view of availability and reactivity, and, particularly, at least one di(meth)acrylate compound (A-2a), represented by the following general formula (A-2a):

$$G\text{-}\{O\text{---}CO\text{---}C(R^4)\text{=}CH_2\}_2 \quad \text{(A-2a)}$$

wherein $R^4$ represents a hydrogen atom or a methyl group and G represents an organic diol compound residue (residue after removing two hydroxyl groups from organic diol compound), is preferably used.

In the general formula (A-2a), the organic diol compound residue G may be any of an aromatic diol compound residue, an aliphatic diol compound residue, and an alicyclic diol compound residue, and it is preferably an aliphatic diol compound residue in view of availability, viscosity, and reactivity.

Specific examples of the di(meth)acrylate compound (A-2a) include di(meth)acrylates of mono or oligoethylene glycols, such as diethylene glycol di(meth)acrylate, triethylene glycol di(meth)acrylate, and tetraethylene glycol di(meth)acrylate; di(meth)acrylates of alkylenediols, such as tetramethylene glycol di(meth)acrylate, pentamethylene di(meth)acrylate, and hexamethylene glycol di(meth)acrylate.

Examples of the above-mentioned polyester (meth)acrylate usable as the other radical polymerizable organic compound (A-2) include polyester (meth)acrylate obtained by the reaction of a hydroxyl group-containing polyester with (meth)acrylic acid.

Examples of the above-mentioned polyether (meth)acrylate include polyether (meth)acrylate obtained by the reaction of a hydroxyl group-containing polyether with (meth)acrylic acid.

To control the treatment of a patient or the artificial tooth worn by the patient and produced by the photocurable resin composition and/or the method of the present invention, the dental photocurable resin composition used in the present invention may contain an inorganic oxide containing an element having X-ray contrast property (heavy metal element) such as barium, strontium, zirconium, bismuth, tungsten, germanium, molybdenum and lanthanide so as to enable a clear confirmation of the mounted state, shape and state of the artificial tooth by an X-ray photograph.

The photocurable resin composition used in the present invention may optionally contain one, or two or more colorant(s) such as pigments and dyes, defoamers, levelling agents, thickeners, flame retardants, antioxidants, curing depth control agents, ultraviolet absorbers, modifier resins, and the like in an appropriate amount as long as the effects of the present invention are not impaired.

When it is used in the stereolithography, the mechanical properties of this photocurable resin composition are dramatically improved if said photocurable resin composition is blended with 10 to 250 parts per weight of a filler (C) per every 100 parts per weight of said photocurable resin composition. Thus, a mixture is obtained comprising the photocurable resin composition and 10-250 phr (parts per hundred resin) of a filler.

In general, it is possible to use, as the filler (C) in the photocurable resin composition according to the present invention, one, two or more inorganic filler(s) and/or organic filler(s).

Non-limiting examples of the inorganic filler include Periodic Table Groups I, II, III, and IV transition metal oxides, chlorides, sulfites, carbonates, phosphates, silicates thereof, or mixtures thereof.

More specific examples thereof include silicon dioxide (silica) powder, aluminium oxide powder (alumina powder), zirconia powder, glass powders such as lantern glass powder, barium glass powder, and strontium glass powder, quartz powder, barium sulphate powder, titanium oxide powder, glass beads, glass fibre, barium fluoride powder, lead salt powder, glass filler containing talc, silica gel powder, colloidal silica, zirconium oxide powder, tin oxide powder, carbon fibre, and other ceramic powder.

Polymer particles can be used as the organic substance filler, and examples thereof include polymethyl methacrylate particles, crosslinked polymethyl methacrylate particles, ethylene-vinyl acetate copolymer particles, styrene-butadiene copolymer particles, acrylonitrile-styrene copolymer particles, ABS resin (acrylonitrile-styrene-butadiene copolymer resin) particles, and the like. Of the above-mentioned fillers, inorganic fillers are preferably used as the filler (C) in view of an improvement in mechanical properties of a cured article (artificial tooth), and suppression of a significant increase in viscosity of the composition. In particular, one, or two or more silica powder(s), alumina powder(s), zirconia powder(s), and glass powder(s) is/are more preferably used in view of mechanical properties and aesthetic property.

Ideally, the average particle diameter of the filler (C) is smaller than a lamination shaping pitch because of limitation in lamination shaping, and is preferably 0.01 to 50 μm, more preferably 0.01 to 25 μm, still more preferably 0.01 to 10 μm, and particularly preferably 0.1 to 5 μm.

The filler (C) preferably has a spherical shape in view of the fact that the viscosity of the dental photocurable resin composition can be reduced, and more preferably it is near a true sphere.

The filler (C) is preferably surface-treated with a silane coupling agent in view of an improvement in mechanical properties of the artificial teeth. Examples of the silane coupling agent include silane coupling agents having reactive functional group such as a (meth)acrylic group, an epoxy group, a vinyl group, an amino group, and a mercapto group, and one, or two or more filler(s) can be used.

The filler is preferably selected from a silica powder, an alumina powder, a zirconia powder, a glass powder, powders prepared by treating the above powders with a coupling agent, and mixtures thereof.

Specific examples of the filler treated with a silane coupling agent usable in the present invention include, but are not limited to, a true spherical silica powder and a true spherical alumina powder (Admafine, manufactured by Admatechs Company Limited) treated with methacrylsilane, a spherical glass powder ("Spheriglass", manufactured by Potters Industries Inc.) and zirconia beads (manufactured by NIIMI SANGYO CO., LTD.) treated with methacrylsilane, and the like.

In case the photocurable resin composition used in the present invention contains a filler (C), the photocurable resin composition (radical polymerizable organic compound (A)+ photosensitive radical polymerization initiator (B)) is blended with 10 to 250 parts per weight of a filler (C) per every 100 parts per weight of the liquid resin composition (A+B).

When the content of the radical polymerizable organic compound (A), the content of the filler (C) and the content of the photosensitive radical polymerization initiator (B) fall within the above range, viscosity and photocuring sensitivity of the photocurable resin composition become very satisfactory when a three-dimensional object reinforced with filler, in particular an artificial tooth, is produced, and strength, abrasion resistance, hardness, low water absorption, aesthetic property, functionality, and the like of the three-dimensional object (artificial tooth) obtained by stereolithography become satisfactory, and also mechanical properties become satisfactory.

More preferably, the photocurable resin composition (radical polymerizable organic compound (A)+photosensitive radical polymerization initiator (B)) is blended with 20 to 200 parts per weight of a filler (C) per every 100 parts per weight of the liquid resin composition (A+B).

This composition is particularly suited when the photocurable resin composition is used for dental application.

The viscosity of the photocurable resin composition is likely to increase when the content of the radical polymerizable organic compound (A) is less than the above-mentioned range, while deterioration of mechanical properties and abrasion resistance of cured article (artificial tooth) is likely to occur when the content is more than the above-mentioned range. Strength, abrasion resistance, hardness, aesthetic property, and the like of the shaped object (artificial tooth) obtained by optical shaping are likely to deteriorate when the content of the filler (C) is less than the above-mentioned range, while the viscosity of the photocurable resin composition significantly increases to cause a significant deterioration of optical shaping property, leading to the deterioration of toughness (durability) of the shaped object (artificial tooth in particular) obtained by optical shaping when the content is more than the above-mentioned range. Sufficient photocuring is less likely to be performed when the content of the photosensitive radical polymerization initiator (B) is less than the above-mentioned range, while mechanical properties of the shaped object (artificial tooth in particular) obtained by optical shaping deteriorate when the content is more than the above-mentioned range.

The radical polymerizable organic compound of the photocurable resin composition of the present invention is preferred to consist only of methacrylate-based compounds.

It is possible to use, as the radical polymerizable organic compound (A) other than the polyrotaxane compound in the photocurable resin composition, any radical polymerizable organic compound as long as it is usable as a photocurable resin material. In view of availability and reactivity, a (meth)acrylic compound having one, or two or more acrylic group(s) and/or methacrylic group(s) in a molecule is preferably used.

The method according to the invention uses the photocurable resin composition in one of the above described embodiments.

In a preferred embodiment of the method according to the invention, the method comprises the following steps:

(a) accommodating said liquid photocurable resin composition in a shaping container having a light permeable bottom face, and irradiating the photocurable resin composition in the shaping container with light in a predetermined shape pattern through the light permeable bottom face of the shaping container in accordance with slice data, every one layer based on three-dimensional CAD data, to form a cured resin layer having a predetermined shape pattern for one layer;

(b) lifting up the cured resin layer for one layer formed during step (a), thereby allowing the liquid photocurable resin composition to flow into the space between the lower face of the cured resin layer and the bottom face of the shaping container, and irradiating the photocurable resin composition between the lower face of the cured resin layer and the bottom face of the shaping container with light in a predetermined shape pattern through the light permeable bottom face of the shaping container in accordance with slice data, every one layer based on three-dimensional CAD data, to further form a cured resin layer having a predetermined shape pattern for one layer, and (c) repeating the operation of step (b) until the desired object is obtained.

By using the photocurable resin composition of the present invention in the stereolithographic method according to the invention, artificial teeth with improved durability are provided.

Stereolithography in which a liquid photocurable resin composition is accommodated in a shaping container having a light permeable bottom face and light is irradiated from the bottom of the container to produce a stereoscopically shaped article is called "regulated liquid surface stereolithography" and it has already been known (JP 4-52042 Y, US 2002/0, 155,189 A). Inventors have described in JP Patent application no. 2013-175277 that, using the regulated liquid surface stereolithography, artificial teeth with excellent aesthetics, hardness, strength, functionality and fit can be produced smoothly and easily in less than one hour.

Furthermore, by using the photocurable resin composition of the present invention containing for example, the (meth) acryl modified polyrotaxane, toughness-and-elasticity-improved artificial teeth with excellent aesthetics, hardness, strength, functionality, and fit can be produced smoothly and easily in short time.

In the shaping container accommodating a liquid dental photocurable resin composition, the entire bottom face may be formed of a light permeable material, or the periphery of the bottom face may be formed of a material which does not transmit light, and also the portion (centre portion) surrounded by the periphery may be formed of a light permeable material, and thus making it possible to decide the area of the light permeable portion in the bottom face according to the maximum size of the artificial tooth produced by each shaping container, corresponding to the maximum area of light to be irradiated through the bottom face of the shaping container, and the like.

It is possible to use, as the material which forms the light permeable bottom face of the shaping container, transparent glass, transparent plastic, and the like. In order to facilitate the peeling of the hardened layer from the transparent container, the transparent release layer of such as fluorine-based rubber and silicone rubber can be applied in the transparent glass and in the transparent plastic.

Ultraviolet ray and visible light, each having a wavelength of 300 to 450 nm, are used as light which is irradiated through the light permeable bottom face of the shaping container. It is possible to use, as light source, a laser beam (for example, semiconductor excitation solid laser capable of emitting ultraviolet light, Ar laser, He—Cd laser, ultraviolet LED laser (light-emitting diode), a LED laser capable of emitting light having a wavelength of 380 to 450 nm), a high-pressure mercury lamp, an ultrahigh-pressure air gun mercury lamp, a low-pressure mercury lamp, a xenon lamp, a halogen lamp, a metal halide lamp, an ultraviolet LED lamp, an ultraviolet fluorescent lamp, and the like. Of these light sources, a LED laser or LED lamp capable of emitting light having a wavelength of about 400 nm (usually about 380 to 410 nm) is preferably used in view of handiness of a device, economy, maintainability, and the like.

In a conventionally used method in which a three-dimensional object is produced by irradiating a photocurable resin composition accommodated in a shaping container with light from the upper surface, optical shaping is usually performed by irradiating with ultraviolet laser beam having a wavelength of 300 to 370 nm, and a light source for emitting ultraviolet laser beam having a wavelength of 300 to 370 nm is generally expensive.

To the contrary, according to the present invention, as mentioned above, it is possible to smoothly produce an artificial tooth which is excellent in aesthetic property, hardness, strength, functionality, fitness, and the like in a short time even by irradiation with light which has lower energy intensity than that of the above ultraviolet laser beam and also has a wavelength of 380 to 450 nm (light in a visible range), and a light source for emitting light having a wavelength of 380 to 450 nm (light in a visible range) is inexpensive and easily available as compared with the light source for emitting ultraviolet laser beam having a wavelength of 300 to 370 nm.

In the case of forming each cured resin layer by irradiating a liquid dental photocurable resin composition accommodated in a shaping container with light through the light permeable bottom face of the shaping container, it is possible to employ a method in which a cured resin layer is formed by irradiating a dental photocurable resin composition with light converted to a spot shape, such as laser beam, through the light permeable bottom face of the shaping container using a line drawing method, or a method in which a cured resin layer is formed by planar irradiation of a dental photocurable resin composition with light passed through a planar drawing mask formed by arranging a plurality of micro-optical shutters such as a liquid crystal shutter or a digital micromirror device (DMD) through the light permeable bottom face of the shaping container.

Advantageously, the three-dimensional CAD data can be a data obtained using a computed tomography device (CT device), a magnetic resonance imaging device (MRI), a computed radiographic device (CR device), or an intraoral 3D scanner.

Another aspect of the invention is a three-dimensional article comprising the photo-cured resin composition according to the invention or obtained by the method according to the invention. In a particularly preferred embodiment of the invention, the three-dimensional article is an artificial tooth.

According to the method of the present invention and using the photocurable resin composition according to the invention, it is possible to produce an artificial tooth used as a provisional tooth for only a short time until a final tooth is mounted (provisional tooth for post crown, provisional tooth for partial false teeth, provisional tooth full set of false teeth), an artificial tooth used as a final tooth (final tooth for post crown, final tooth for partial false teeth, final tooth for full set of false teeth), a denture for training of dental student, and the like in a short time, simply and smoothly.

However, before the inventors idea there has never been produced an artificial tooth using a regulated liquid surface stereolithography using a photocurable resin composition according to the invention. The method proposed here enables the user to produce an artificial tooth in less than one hour, a timing that is impossible with known photocurable resin compositions and irradiating from the upper surface with an optical shaping method.

It is estimated that the liquid dental photocurable resin composition flowed into the regulated space between the lower face of the cured resin layer and the bottom face of the shaping container is cured by light irradiated through the bottom face without being exposed to air, and thus curing inhibition due to oxygen does not occur and photocuring is performed quickly and surely.

According to the present invention, it is possible to produce a three-dimensional object useful for design verification or performance check for development and manufacture of industrial products, like hearing aids or nursing care and also an artificial tooth which has various properties required for an artificial tooth, such as strength, abrasion resistance, hardness, and low water absorption, and which is also excellent in aesthetic property and functionality and producible in a short time, smoothly and simply, using a liquid photocurable resin composition according to the invention containing a specific polyrotaxane compound, a radical polymerizable organic compound, a photosensitive radical polymerization initiator, and, preferably, a filler.

Further, according to one of the aspects of the present invention, it is possible to simply produce in a short time an artificial tooth which has various properties required to the artificial tooth, such as strength, abrasion resistance, hardness, and low water absorption, and is also excellent in aesthetic property and functionality using the above-mentioned photocurable resin composition and the method according to the invention, without being influenced by the degree of proficiency level of skill of a dentist or a dental technician.

Furthermore, according to the method and the resin composition of the present invention, it is possible to smoothly produce a three-dimensional object which is excellent in appearance, hardness, strength and functionality in a significantly short time even when using an inexpensive light source capable of emitting light having a wavelength of 380 to 450 nm (light in a visible range) without using an expensive light source capable or emitting ultraviolet laser beam having a wavelength of 300 to 370 nm which is usually used when a stereoscopically shaped article is produced by emitting light from the upper surface of a photocurable resin composition.

Variant embodiments of the invention are the subject of the dependent claims. The description of preferred embodiments of the resin composition and the method according to the invention is provided in the following pages by way of non-limiting examples.

DESCRIPTION OF PREFERRED EXAMPLE EMBODIMENTS OF THE INVENTION

In the present invention, a liquid photocurable resin composition containing a radical polymerizable organic compound (A) which contains a polyrotaxane compound with a photo-polymerizable group and a photosensitive radical polymerization initiator (B) and preferably a filler (C) is used as the material for the production of a three-dimensional object with high toughness and high elasticity.

A (meth)acryl modified polyrotaxane according to the invention can be derived from a polyrotaxane compound containing cyclodextrin or hydroxypropylized cyclodextrin rings wherein one or more hydroxyl groups of the cyclodextrin ring and/or the hydroxyl group of hydroxypropyl are derivatized with ε-caprolactone in a first step and then in a second step with $CH_2=C(R^1)CO_2(CH_2)_2NCO$ wherein $R^1$ represents a hydrogen atom or a methyl group. More specifically, the polyrotaxane compound can be obtained using the methods disclosed in document JP 2011-046917, those derived from the reaction of hydroxyalkyl polyrotaxane and 2-acryloyloxyethyl isocyanate and the like.

In particular, as (meth)acryl modified polyrotaxane compound in this sense, various molecular weight compounds are commercially available from Advanced Softmaterials Inc., such as SM3405P, SM2400P, SM1315P, SA3405P, SA2405P and SA1315P which contain solvent.

There are other products without solvent but with low molecular weight light cross-linking monomer in order to adjust the reactivity or viscosity, such as SM3400C, SA3400C, SA2400C, SA1310C, SM2400C, SM1310C, etc.

Among these, SM type is a methacryl modified type and SA type is an acryl modified product. The molecular weights of these modified polyrotaxane are: 34 series are about 35,000, 24 series are about 20,000, 13 series are about 11,000. These molecular weights are determined by the ring number of compounds such as cyclodextrins and the length of the straight-chain polymer. Here, an example of Advanced Softmaterials Inc. is shown but the object of the present invention can be achieved also by other polymerizable derivatives of polyrotaxane in the sense of the invention.

The present invention will be specifically described below by way of Examples, but the present invention is not limited to the following Examples.

Example 1

(1) 10.0 g of a mixture of cross-linkable oligomer and methacryl modified polyrotaxane ("SeRM Key Mixture SM1310C" manufactured by Advanced Softmaterials Inc.), 80.0 g of urethane dimethacrylate ("U-2TH", manufactured by Shin Nakamura Chemical Co., Ltd.) obtained by the reaction of 1 mol of 2,2,4-trimethyl-hexamethylene diisocyanate with 2 mol of 2-hydroxyethyl methacrylate, which is represented by the formula "$CH_2=C(CH_3)-CO-O-CH_2CH_2-O-CO-NH-[CH_2C(CH_3)_2CH_2CH(CH_3)CH_2CH_2]-NH-CO-O-CH_2CH_2-O-CO-(CH_3)C=CH_2$", 20 g of triethylene glycol dimethacrylate ("NK-3G", manufactured by Shin Nakamura Chemical Co., Ltd.), and 1.1 g of 2,4,6-trimethylbenzoyl-diphenyl-phosphine oxide ("Irgacure TPO", photosensitive radical polymerization initiator, manufactured by BASF Corporation) were mixed, followed by stirring to prepare a liquid photocurable resin composition. Using a B type viscometer ("DV-E", manufactured by Brookfield Engineering Laboratories, Inc.), the viscosity of the thus obtained photocurable resin composition was measured at 25° C. The result was of 1,200 mPa·s.

(2) Using the liquid photocurable resin composition obtained in the above (1), optical shaping was performed by a regulated liquid surface stereolithography device of a type in which light is irradiated from the bottom side through the light permeable bottom face of a shaping container using a line drawing system ("DigitalWax 029D", manufactured by DWS SRL) under the conditions of a laser output of 30 mW, a wavelength of 405 nm, a beam diameter of 0.02 mm, a laser operation rate of 4,600 mm/sec, and a one layer thickness of 0.05 mm in accordance with slice data, every one layer based on three-dimensional CAD data, relating to a bar in accordance with ISO 180 and then the impact strength property was measured in accordance with ISO 180 using a measuring device manufactured by Galdabini (Impact 150).

(3) Using the liquid photocurable resin composition obtained in the above (1), dumbbells and bars for the measurement of tensile property and bending property were produced by the regulated liquid surface stereolithography device (DigitalWax 029D) used in the above (2) under the same conditions as in the above (2) in accordance with ISO 527-2 and ISO 178, and then tensile property and bending property were measured in accordance with ISO 527-2 and ISO 178 using a measuring device manufactured by Shimadzu Corporation (AutoGraph AG-XPlus).

Using ASKER, Model D, manufactured by KOBUNSHI KEIKI CO., LTD., surface hardness was measured as Shore D hardness.

The results are shown in Table 1 below.

Example 2

(1) 20.0 g of mixture of cross-linkable oligomer and methacryl modified polyrotaxane ("SeRM Key Mixture SM1310C" manufactured by Advanced Softmaterials Inc.), 80.0 g of urethane dimethacrylate ("U-2TH", manufactured by Shin Nakamura Chemical Co., Ltd.) obtained by the reaction of 1 mol of 2,2,4-trimethyl-hexamethylene diisocyanate with 2 mol of 2-hydroxyethyl methacrylate, which is represented by the formula "$CH_2=C(CH_3)-CO-O-CH_2CH_2-O-CO-NH-[CH_2C(CH_3)_2CH_2CH(CH_3)CH_2CH_2]-NH-CO-O-CH_2CH_2-O-CO-(CH_3)C=CH_2$", 20 g of triethylene glycol dimethacrylate ("NK-3G", manufactured by Shin Nakamura Chemical Co., Ltd.), and 1.2 g of 2,4,6-trimethylbenzoyl-diphenyl-phosphine oxide ("Irgacure TPO", photosensitive radical polymerization initiator, manufactured by BASF Corporation) were mixed, followed by stirring to prepare a liquid photocurable resin composition. Using a B type viscometer ("DV-E", manufactured by Brookfield Engineering Laboratories, Inc.), the viscosity of the thus obtained photocurable resin composition was measured at 25° C. The result was of 1,740 mPa·s.

(2) Using the liquid photocurable resin composition obtained in the above (1), three-dimensional objects were produced in the same manner as in Example 1, (2) and (3), and then various physical properties were determined in the same manner as in Example 1, (2) and (3), to obtain the results as shown in the following Table 1.

Example 3

(1) 10.0 g of mixture of cross-linkable oligomer and methacryl modified polyrotaxane ("SeRM Key Mixture SM1310C" manufactured by Advanced Softmaterials Inc.), 80.0 g of urethane dimethacrylate ("U-2TH", manufactured by Shin Nakamura Chemical Co., Ltd.) obtained by the reaction of 1 mol of 2,2,4-trimethyl-hexamethylene diisocyanate with 2 mol of 2-hydroxy-ethyl methacrylate, which is represented by the formula "$CH_2=C(CH_3)-CO-O-CH_2CH_2-O-CO-NH-[CH_2C(CH_3)_2CH_2CH(CH_3)CH_2CH_2]-NH-CO-O-CH_2CH_2-O-CO-(CH_3)C=CH_2$", 20 g of triethylene glycol dimethacrylate ("NK-3G", manufactured by Shin Nakamura Chemical Co., Ltd.), and 1.1 g of 2,4,6-trimethylbenzoyl-diphenyl-phosphine oxide ("Irgacure TPO", photosensitive radical polymerization initiator, manufactured by BASF Corporation) were mixed, followed by stirring to prepare a liquid photocurable resin, and then the mixture was mixed with 60.0 g of a methacrylsilane-treated silica powder ("Admafine SO-C1", average particle diameter of 0.25 μm, manufactured by Admatechs Company Limited) to prepare a liquid photocurable resin composition.

Using a B type viscometer ("DV-E", manufactured by Brookfield Engineering Laboratories, Inc.), the viscosity of the thus obtained photocurable resin composition was measured at 25° C. The result was of 2,560 mPa·s.

(2) Using the liquid photocurable resin composition obtained in the above (1), optical shaping was performed by the same regulated liquid surface stereolithography device used in Example 1, (2) under the same conditions as in Example 1, (2) to produce an artificial tooth for three true teeth (height of 13.1 mm) over 35 minutes.

(3) After removing a supporting member from the artificial tooth obtained in the above (2) and washing with ethanol, and further post exposing for 20 minutes using a post exposure device (post exposure device "UV curing unit S2", manufactured by DWS SRL), a surface was simply ground and polished to produce an artificial tooth, and this artificial tooth was used for the patient as a provisional tooth.

(4) Using the liquid photocurable resin composition obtained in the above (1), dumbbells and bars for the measurement of tensile property and bending property were produced by the regulated liquid surface stereolithography device (DigitalWax 029D) used in the above (2) under the same conditions as in the above (2) in accordance with ISO 527-2 and ISO 178, and then tensile property and bending property were measured in accordance with ISO 527-2 and ISO 178 using a measuring device manufactured by Shimadzu Corporation (AutoGraph AG-XPlus).

In the same manner also the bars in accordance with ISO 180 were produced and then the impact strength property was measured in accordance with ISO 180 using a measuring device manufactured by Galdabini (Impact 150).

Using ASKER, Model D, manufactured by KOBUNSHI KEIKI CO., LTD., surface hardness was measured as Shore D hardness.

The results are shown in Table 1 below.

Example 4

(1) 20.0 g of mixture of cross-linkable oligomer and methacryl modified polyrotaxane ("SeRM Key Mixture SM1310C" manufactured by Advanced Softmaterials Inc.), 80.0 g of urethane dimethacrylate ("U-2TH", manufactured by Shin Nakamura Chemical Co., Ltd.) obtained by the reaction of 1 mol of 2,2,4-trimethyl-hexamethylene diisocyanate with 2 mol of 2-hydroxy-ethyl methacrylate, which is represented by the formula "$CH_2=C(CH_3)-CO-O-CH_2CH_2-O-CO-NH-[CH_2C(CH_3)_2CH_2CH(CH_3)CH_2CH_2]-NH-CO-O-CH_2CH_2-O-CO-(CH_3)C=CH_2$", 20 g of triethylene glycol dimethacrylate ("NK-3G", manufactured by Shin Nakamura Chemical Co., Ltd.), and 1.2 g of 2,4,6-trimethylbenzoyl-diphenyl-phosphine oxide ("Irgacure TPO", photosensitive radical polymerization initiator, manufactured by BASF Corporation) were mixed, followed by stirring to prepare a liquid photocurable resin, and then the mixture was mixed with 60.0 g of a methacrylsilane-treated silica powder ("Admafine SO-C1", average particle diameter of 0.25 μm, manufactured by Admatechs Company Limited) to prepare a liquid photocurable resin composition.

Using a B type viscometer ("DV-E", manufactured by Brookfield Engineering Laboratories, Inc.), the viscosity of the thus obtained photocurable resin composition was measured at 25° C. The result was of 7,620 mPa·s.

(2) Using the liquid photocurable resin composition obtained in the above (1), optical shaping was performed by the same regulated liquid surface stereolithography device used in Example 1, (2) under the same conditions as in Example 1, (2) to produce an artificial tooth for three true teeth (height of 13.1 mm) over 35 minutes.

(3) After removing a supporting member from the artificial tooth obtained in the above (2) and washing with ethanol, and further post exposing for 20 minutes using a post exposure device (post exposure device "UV curing unit S2", manufactured by DWS SRL), a surface was simply ground and polished to produce an artificial tooth, and this artificial tooth was used for the patient as a provisional tooth.

(4) Using the liquid photocurable resin composition obtained in the above (1), dumbbells and bars for the measurement of tensile property and bending property were produced by the regulated liquid surface stereolithography device (DigitalWax 029D) used in the above (2) under the same conditions as in the above (2) in accordance with ISO 527-2 and ISO 178, and then tensile property and bending property were measured in accordance with ISO 527-2 and ISO 178 using a measuring device manufactured by Shimadzu Corporation (AutoGraph AG-XPlus).

In the same manner also the bar in accordance with ISO 180 was produced and then the impact strength property was measured in accordance with ISO 180 using a measuring device manufactured by Galdabini (Impact 150). Using ASKER, Model D, manufactured by KOBUNSHI KEIKI CO., LTD., surface hardness was measured as Shore D hardness.

The results are shown in Table 1 below.

Comparative Example 1

(1) 80.0 g of urethane dimethacrylate ("U-2TH", manufactured by Shin Nakamura Chemical Co., Ltd.) obtained by the reaction of 1 mol of 2,2,4-trimethylhexamethylene diisocyanate with 2 mol of 2-hydroxyethyl methacrylate, which is represented by the formula "$CH_2=C(CH_3)-CO-O-CH_2CH_2-O-CO-NH-[CH_2C(CH_3)_2CH_2CH(CH_3)CH_2CH_2]-NH-CO-O-CH_2CH_2-O-CO-(CH_3)C=CH_2$", 20 g of triethylene glycol dimethacrylate ("NK-3G", manufactured by Shin Nakamura Chemical Co., Ltd.), and 1.0 g of 2,4,6-trimethylbenzoyl-diphenyl-phosphine oxide ("Irgacure TPO", photosensitive radical polymerization initiator, manufactured by BASF Corporation) were mixed, followed by stirring to prepare a liquid photocurable resin composition. Using a B type viscometer ("DV-E", manufactured by Brookfield Engineering Laboratories, Inc.), the viscosity of the thus obtained photocurable resin composition was measured at 25° C. The result was of 750 mPa·s.

(2) Using the liquid photocurable resin composition obtained in the above (1), three-dimensional objects were produced in the same manner as in Example 1, (2) and (3), and then various physical properties were determined in the same manner as in Example 1, (2) and (3), to obtain the results as shown in the following Table 1.

Comparative Example 2

(1) 80.0 g of urethane dimethacrylate ("U-2TH", manufactured by Shin Nakamura Chemical Co., Ltd.) obtained by the reaction of 1 mol of 2,2,4-trimethylhexamethylene diisocyanate with 2 mol of 2-hydroxyethyl methacrylate, which is represented by the formula "$CH_2=C(CH_3)-CO-O-CH_2CH_2-O-CO-NH-[CH_2C(CH_3)_2CH_2CH(CH_3)CH_2CH_2]-NH-CO-O-CH_2CH_2-O-CO-(CH_3)C=CH_2$", 20 g of triethylene glycol dimethacrylate ("NK-3G", manufactured by Shin Nakamura Chemical Co., Ltd.), and 1.0 g of 2,4,6-trimethylbenzoyl-diphenyl-phosphine oxide ("Irgacure TPO", photosensitive radical polymerization initiator, manufactured by BASF Corporation) were mixed, followed by stirring to prepare a liquid photocurable resin, and then the mixture was mixed with 60.0 g of a methacrylsilane-treated silica powder ("Admafine SO-C1", average particle diameter of 0.25 μm, manufactured by Admatechs Company Limited) to prepare a liquid photocurable resin composition.

Using a B type viscometer ("DV-E", manufactured by Brookfield Engineering Laboratories, Inc.), the viscosity of the thus obtained photocurable resin composition was measured at 25° C. The result was of 1,360 mPa·s.

(2) Using the liquid photocurable resin composition obtained in the above (1), three-dimensional objects were produced in the same manner as in Example 1, (2) and (3), and then various physical properties were determined in the same manner as in Example 1, (2) and (3) to obtain the results as shown in the following Table 1.

TABLE 1

| Parameter | Method | Example 1 | Example 2 | Example 3 | Example 4 | Comparative Example 1 | Comparative Example 2 |
|---|---|---|---|---|---|---|---|
| Viscosity of dental photocurable resin composition (mPa · s) (25° C.) | ISO 2555 | 1200 | 1740 | 2560 | 7620 | 750 | 1360 |
| Tensile strength (MPa) of cured material | ISO 527-2-1BA | 39.5 | 32.9 | 56.1 | 57.5 | 34.1 | 48.5 |
| Tensile modulus (MPa) of cured material | ISO 527-2-1BA | 1510 | 1200 | 3248 | 3413 | 1320 | 3430 |
| Flexural strength (MPa) of cured material | ISO 178 | 67.6 | 64.8 | 102 | 107 | 63.5 | 87 |
| Flexural modulus (MPa) of cured material | ISO 178 | 1420 | 1440 | 2960 | 3025 | 1360 | 3060 |
| Surface hardness (Shore D) of cured material | ISO 868 | 85 | 86 | 92 | 92 | 85 | 92 |
| Izod impact strength (J/m) of cured material | ISO 180 | 136.1 | 263.9 | 106 | 235 | 82.5 | 86 |

As shown by the results indicated in the Table 1 above, the shaped objects obtained in the Examples 1 to 4 can be effectively used as artificial teeth or prototypes thanks to their sufficient surface hardness, tensile strength, tensile modulus, flexural modulus and flexural strength, as well as to their high toughness.

A practical artificial tooth cannot be produced in a short optical shaping time when the artificial tooth is produced by irradiating the upper surface of a dental photocurable resin composition with light in accordance with an optical shaping method which has most widely been employed heretofore.

The invention has a wide industrial applicability. According to a method of the present invention for producing a three-dimensional object and using the resin composition according to the invention, it is possible to produce a three-dimensional object, for example an artificial tooth, which is excellent in aesthetic property, hardness, strength, functionality, fitness, and the like in a short time, simply and smoothly, without requiring skill.

Upon implementation, the method, the photocurable resin composition and the three-dimensional article that are the subjects of the invention can be subjected to further modifications and variant embodiments can be obtained that are not described herein. Said modifications or variants must all be considered protected by the present patent, provided that they fall within the scope of the claims expressed below.

The invention claimed is:

1. Method for producing a three-dimensional object by stereolithography wherein a liquid photocurable resin composition is cured by light, said photocurable resin composition containing:

(i) from 90 to 99.9% by weight, based on the total weight of the photocurable resin composition, of a radical polymerizable organic compound (A) selected from radical polymerizable monomers, oligomers, pre-polymers and mixtures thereof;

(ii) from 0.1 to 10% by weight, based on the total weight of the photocurable resin composition, of a photosensitive radical polymerization initiator (B);

wherein said radical polymerizable organic compound (A) comprises, based on the weight of the radical polymerizable organic compound (A), from 0.5 to 20% by weight of a polyrotaxane compound having the following general formula (I):

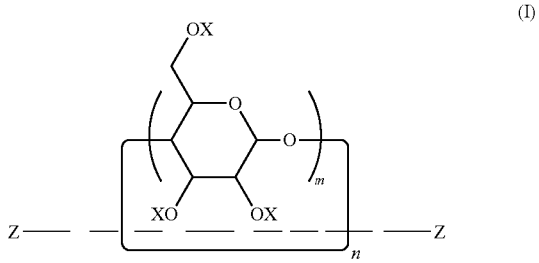

wherein

Z is a bulky capping group;

the dotted ------ line is a polymer chain selected from the group consisting of polyethylene glycol (PEG), polypropylene glycol (PPG), polyethylene glycol-polypropylene glycol (PEG-PPG) block copolymer or polydimethylsiloxane (PDMS), onto which at least one cyclodextrin ring is slipped;

m is an integer and independently represents the number of glucose units in the at least one cyclodextrin ring;

n is an integer and represents the number of cyclodextrin rings;

X is independently H, or a radical polymerizable group, selected from: a methacryloyl-containing group or an acryloyl-containing group, with the condition that at least one X is a radical polymerizable group.

2. The method according to claim 1, further comprising:

(a) accommodating said liquid photocurable resin composition in a shaping container having a light permeable bottom face, and irradiating the photocurable resin composition in the shaping container with light in a predetermined shape pattern through the light permeable bottom face of the shaping container in accordance with slice data, every one layer based on three-dimensional CAD data to form a cured resin layer having a predetermined shape pattern for one layer;

(b) lifting up the cured resin layer for one layer formed during step (a), thereby allowing the liquid photocurable resin composition to flow into the space between the lower face of the cured resin layer and the bottom face of the shaping container, and irradiating the photocurable resin composition between the lower face of the cured resin layer and the bottom face of the shaping container with light in a predetermined shape pattern through the light permeable bottom face of the shaping container in accordance with slice data, every one layer based on three-dimensional CAD data to form a further cured resin layer having a predetermined shape pattern for one layer, and (c) repeating the operation of step (b) until the desired object is obtained.

3. The method according to claim 2, wherein the three-dimensional CAD data are obtained using a computed tomography device (CT device), a magnetic resonance imaging device (MRI), a computed radiographic device (CR device), or an intraoral 3D scanner.

4. The method according to claim 1, wherein the radical polymerizable group of said liquid photocurable resin composition is constituted by a methacryloyl or acryloyl-containing unit bonded by a spacer unit to said cyclodextrin ring.

5. The method for producing a three-dimensional object according to claim 1, wherein said three-dimensional object is an artificial tooth.

6. The method according to claim 1, wherein said radical polymerizable group is independently selected from

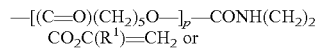

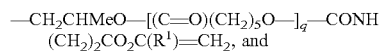

wherein $R^1$ represents a hydrogen atom or a methyl group with p and q being integers indicating the number of repeating units.

7. The method according to claim 1, wherein said radical polymerizable organic compound (A) further comprises:

(i) a urethane-based di(meth)acrylate compound (A-1a) obtained by the reaction of 1 mol of an organic diisocyanate compound with 2 mol of hydroxyalkyl (meth) acrylate, represented by the following general formula (A-1a):

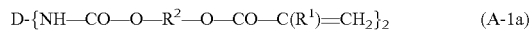

wherein $R^1$ represents a hydrogen atom or a methyl group, $R^2$ represents an alkylene group, and D represents an organic diisocyanate compound residue; and/or (ii) a di(meth)acrylate compound (A-1b) obtained by the reaction of 1 mol of a diepoxy compound with 2 mol of (meth)acrylic acid, represented by the following general formula (A-1 b):

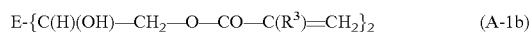

wherein $R^3$ represents a hydrogen atom or a methyl group, and E represents a diepoxy compound residue.

8. The method according to claim 1, wherein the viscosity of said photocurable resin composition is 20,000 mPa·s or less, when measured at 25° C. according to method ISO 2555 with a single cylinder rotational viscometer.

9. The method according to claim 1, wherein every radical polymerizable organic compound (A) is a methacrylate-based compound.

10. The method according to claim 1, wherein in said polyrotaxane compound the polymer chain is polyethylene glycol, the cyclodextrin is acyclodextrin and the bulky groups are —NH-adamantane.

11. The method according to claim 1, wherein said radical polymerizable organic compound (A) further includes a viscosity reducing compound (A-2) which is at least one of: a methacrylic acid ester, an acrylic acid ester, a polyester methacrylate, a polyester acrylate, a polyether methacrylate of alcohols, or a polyether acrylate of alcohols.

12. The method according to claim 7, wherein said radical polymerizable organic compound (A) comprises radical polymerizable monomers that are not the polyrotaxane compound or compounds (A-1a), (A-1b) and (A-2).

13. The method according to claim 1, wherein said photocurable resin composition is blended with 10 to 250 parts per weight of a filler (C) per every 100 parts per weight of said photocurable resin composition.

14. The method according to claim 13, wherein said filler (C) is selected from a silica powder, an alumina powder, a zirconia powder, a glass powder, powders prepared by treating the above powders with a coupling agent, and mixtures thereof.

15. The method according to claim 1, wherein Z is selected from adamantine; adamantine derivatives; 2,4-dinitrophenyl; cyclodextrin; or cyclodextrin derivatives.

16. The method according to claim 1, wherein m=6, 7 or 8.

17. The method according to claim 8, wherein the viscosity of said photocurable resin composition is 15,000 mPa·s or less, when measured at 25° C. according to method ISO 2555 with a single cylinder rotational viscometer.

18. The method according to claim 17, wherein the viscosity of said photocurable resin composition is 10,000 mPa·s or less, when measured at 25° C. according to method ISO 2555 with a single cylinder rotational viscometer.

\* \* \* \* \*